(12) United States Patent
Bennert (10) Patent No.: US 10,697,690 B2
(45) Date of Patent: Jun. 30, 2020

(54) ICE MACHINE CLEANING SYSTEM AND METHOD OF USE (71) Applicant: Jon Bennert, Armarillo, TX (US)

(72) Inventor: Jon Bennert, Armarillo, TX (US)

(73) Assignee: Air Oasis LLC, Amarillo, TX (US)

( * ) Notice: Subject to any disclaimer, the term of this patent is extended or adjusted under 35 U.S.C. 154(b) by 78 days.

(21) Appl. No.: 16/183,539

(22) Filed: Nov. 7, 2018

(65) Prior Publication Data

US 2019/0137165 A1 May 9, 2019

Related U.S. Application Data

(60) Provisional application No. 62/582,758, filed on Nov. 7, 2017.

(51) Int. Cl.
*F25D 17/04* (2006.01)
*A61L 2/14* (2006.01)
*F25C 1/00* (2006.01)
*A61L 9/22* (2006.01)

(52) U.S. Cl.
CPC ............. *F25D 17/042* (2013.01); *A61L 2/14* (2013.01); *F25C 1/00* (2013.01); *A61L 9/22* (2013.01); *F25C 2400/12* (2013.01); *F25D 2317/0416* (2013.01)

(58) Field of Classification Search
CPC .. F25D 17/042; F25D 2317/0416; A61L 2/14; A61L 9/22; F25C 1/00; F25C 2400/12
See application file for complete search history.

(56) References Cited

U.S. PATENT DOCUMENTS

2014/0029155 A1* 1/2014 Waddell ................. H01T 23/00
361/231

* cited by examiner

*Primary Examiner* — Emmanuel E Duke
(74) *Attorney, Agent, or Firm* — Shannon Warren (57) ABSTRACT

An surface sanitizing system for cleaning a portion of an ice machine with a bipolar ions, wherein, said surface sanitizing system comprises a plugs, a power lines, an ion generation power module, a two or more brush cables, a two brushes a brush container and a mounting clip. Said plugs selectively attaches to a power source and provides electricity for running said surface sanitizing system. Said power lines selectively attach said plugs to said ion generation power module. Said two or more brush cables selectively attach said ion generation power module to said two brushes. A female containment portions selectively holds said two brushes within a portion of said brush container. Said two brushes selectively attach to a portion of said two or more brush cables. Said brush container selectively clips into said mounting clip. Said mounting clip selectively attaches to a portion of an ice maker.

9 Claims, 12 Drawing Sheets

ICE MACHINE CLEANING SYSTEM AND METHOD OF USE

CROSS-REFERENCE TO RELATED APPLICATIONS

This application claims benefit to U.S. Patent Application No. 62/582,758 filed on Nov. 7, 2017.

STATEMENT REGARDING FEDERALLY SPONSORED RESEARCH OR DEVELOPMENT (IF APPLICABLE)

Not applicable.

REFERENCE TO SEQUENCE LISTING, A TABLE, OR A COMPUTER PROGRAM LISTING COMPACT DISC APPENDIX (IF APPLICABLE)

Not applicable.

BACKGROUND OF THE INVENTION

Prior art known to the Applicant includes U.S. Pat. No. 8,564,924 B1; U.S. Pat. No. 9,025,303 B2; US 20170232131 A1; US 20170040149 A1; US 20100223944 A1

None of the known inventions and patents, taken either singularly or in combination, is seen to describe the instant disclosure as claimed.

BRIEF SUMMARY OF THE INVENTION

An surface sanitizing system for cleaning a portion of an ice machine with a bipolar ions, wherein, said surface sanitizing system comprises a plugs, a power lines, an ion generation power module, a two or more brush cables, a two brushes a brush container and a mounting clip. Said plugs selectively attaches to a power source and provides electricity for running said surface sanitizing system. Said power lines selectively attach said plugs to said ion generation power module. Said two or more brush cables selectively attach said ion generation power module to said two brushes. A female containment portions selectively holds said two brushes within a portion of said brush container. Said two brushes selectively attach to a portion of said two or more brush cables. Said brush container selectively clips into said mounting clip. Said mounting clip selectively attaches to a portion of an ice maker. Said surface sanitizing system comprising a one or more steps comprising installing said mounting clip into a portion of said ice machine, installing a portion of said two brushes into said brush container, attaching said two brushes to said two or more brush cables, said two or more brush cables to said ion generation power module, said ion generation power module to said power lines, said power lines to said plugs, and said plugs to said power source, energizing said plugs with said power source, emitting said bipolar ions with said two brushes into a portion of said ice machine, and preventing the spread of unwanted bacteria, fungus, and yeast within a portion of said ice machine with said bipolar ions.

An surface sanitizing system for cleaning a portion of an ice machine with a bipolar ions, wherein, said surface sanitizing system comprises a plugs, a power lines, an ion generation power module, a two or more brush cables, a two brushes and a mounting clip. Said plugs selectively attaches to a power source and provides electricity for running said surface sanitizing system. Said power lines selectively attach said plugs to said ion generation power module. Said two or more brush cables selectively attach said ion generation power module to said two brushes. Said two brushes selectively attach to a portion of said two or more brush cables.

An ice machine cleaning method for cleaning a portion of an ice machine with a bipolar ions generated by an surface sanitizing system. Comprising installing a mounting clip of said surface sanitizing system into a portion of said ice machine. Installing a portion of a two brushes into a brush container. Attaching said two brushes to a two or more brush cables, said two or more brush cables to an ion generation power module, said ion generation power module to a power lines, said power lines to a plugs, and said plugs to a power source. Energizing said plugs with said power source. Emitting said bipolar ions with said two brushes into a portion of said ice machine. Preventing the spread of unwanted bacteria, fungus, and yeast within a portion of said ice machine with said bipolar ions. Wherein said surface sanitizing system comprises said plugs, said power lines, said ion generation power module, said two or more brush cables, said two brushes said brush container and said mounting clip. Wherein said plugs selectively attaches to said power source and provides electricity for running said surface sanitizing system. Wherein said power lines selectively attach said plugs to said ion generation power module. Wherein said two or more brush cables selectively attach said ion generation power module to said two brushes. Wherein a female containment portions selectively holds said two brushes within a portion of said brush container. Wherein said mounting clip selectively attaches to a portion of an ice maker.

DETAILED DESCRIPTION OF THE INVENTION

The following description is presented to enable any person skilled in the art to make and use the invention as claimed and is provided in the context of the particular examples discussed below, variations of which will be readily apparent to those skilled in the art. In the interest of clarity, not all features of an actual implementation are described in this specification. It will be appreciated that in the development of any such actual implementation (as in any development project), design decisions must be made to achieve the designers' specific goals (e.g., compliance with system- and business-related constraints), and that these goals will vary from one implementation to another. It will also be appreciated that such development effort might be complex and time-consuming, but would nevertheless be a routine undertaking for those of ordinary skill in the field of the appropriate art having the benefit of this disclosure. Accordingly, the claims appended hereto are not intended to be limited by the disclosed embodiments, but are to be accorded their widest scope consistent with the principles and features disclosed herein.

These parts are illustrated in the figures and discussed below:
a surface sanitizing system 100
a brush container 102
a female containment portions 104
a first female containment portion 104a
a second female containment portion 104b
a mounting clip 106
a two brushes 108
a first brush 108a
a second brush 108b
a two or more brush cables 110
a first brush cable 110a
a second brush cable 110b
an ion generation power module 112
a power lines 114
a plugs 116
a first plug 116a
a second plug 116b
an ice machine 200
an ice maker 202
an ice reservoir 204
an ice 206
a power source 208
a bipolar ions 210
an air purifier 212
an air in 214
an air out 216
a plugs 302
a first plug 302a
a second plug 302b
a sockets 304
a first socket 304a
a second socket 304b
a two sides 306
a first side 306a
a second side 306b
a brushes 308
a first brush 308a
a second brush 308b
a bridge 310
a sockets 400
a first socket 400a
a second socket 400b
a brush sockets 402
a first brush socket 402a
a second brush socket 402b
an emission sockets 404
a first emission socket 404a
a second emission socket 404b
a width 406
a width 408
a length 410
a socket width 412
a socket height 414
a height 416
a stops 418
a brush containment portion 600
a line containment portion 602
a brush aperture 604
a line aperture 606
a grip 608
a first end 610
a second end 612
a neck 614
a width 616
a width 618
a length 620
a width 622
a height 624
a height 626
a width 628
a diameter 630
a base 800
a clip body 802
a bridge 804
a clip head 806
a clip enclosure 900
an enclosure bump 902
a bottom surface 904
a top surface 906
a wires 1000
a first wire 1000a
a second wire 1000b
an inline fuse 1002
an ice machine cleaning method 1100
a one or more steps 1102
a first step 1102a
a second step 1102b
a third step 1102c
a fourth step 1102d
a fifth step 1102e
a sixth step 1102f a performance summary chart 1200 a colonies without cleaning system 1202 a colonies with cleaning system 1204

Figure 1A:
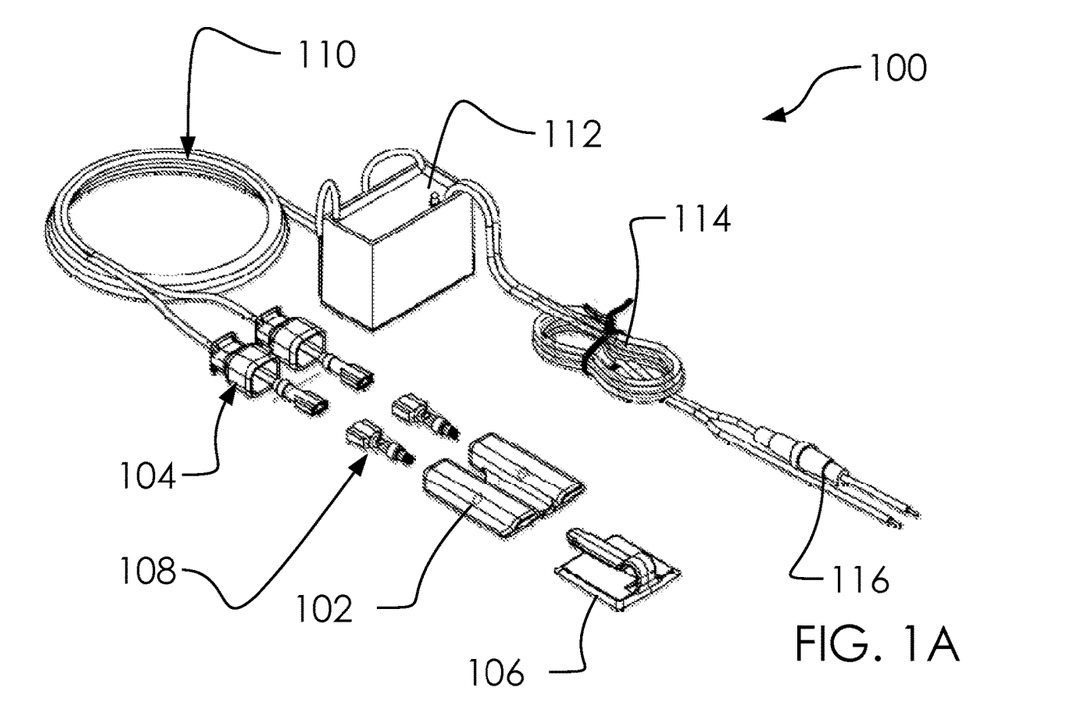
FIG. 1A illustrates a perspective overview view of surface sanitizing system 100.

FIG. 1A illustrates a perspective overview view of surface sanitizing system 100.

Figure 1B:
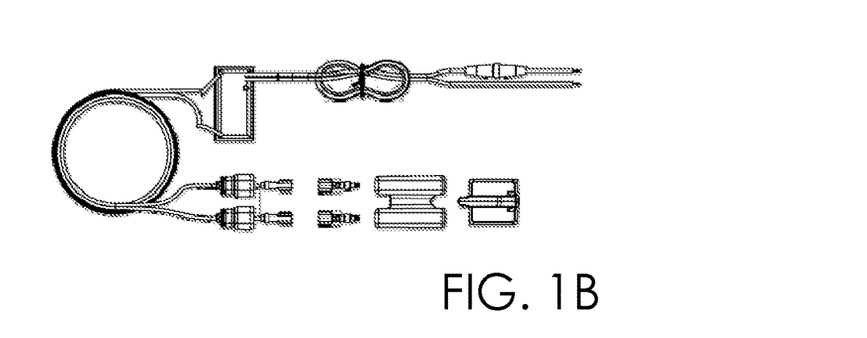
FIG. 1B illustrates an elevated top side view of surface sanitizing system 100.

FIG. 1B illustrates an elevated top side view of surface sanitizing system 100.

Figure 1C:
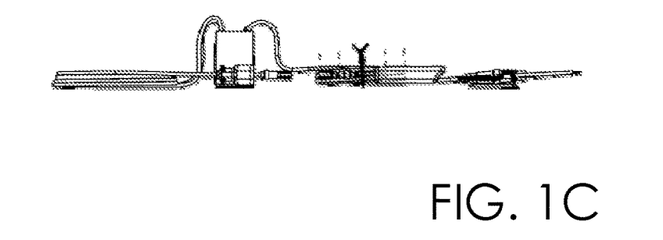
FIGS. 1C and 1D illustrate an elevated front side view and an elevated first side view of surface sanitizing system 100.
Figure 1D:
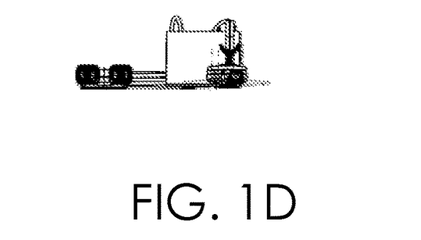

FIGS. 1C and 1D illustrate an elevated front side view and an elevated first side view of surface sanitizing system 100.

In one embodiment, said surface sanitizing system 100 can comprise said brush container 102, said brush container 102, said female containment portions 104, said mounting clip 106, said mounting clip 106, said two brushes 108, said second brush 108*b*, said two or more brush cables 110, said ion generation power module 112, said power lines 114, said power lines 114 and said plugs 116.

In one embodiment, said female containment portions 104 can comprise said first female containment portion 104*a* and said second female containment portion 104*b*.

In one embodiment, said two brushes 108 can comprise said first brush 108*a* and said second brush 108*b*.

In one embodiment, said two or more brush cables 110 can comprise said first brush cable 110*a* and said second brush cable 110*b*.

In one embodiment, said plugs 116 can comprise said first plug 116*a* and said second plug 116*b*.

In one embodiment, surface sanitizing system 100 can be used for cleaning said ice maker 202, as discussed below.

Said surface sanitizing system 100 can comprise one or more features designed for use in a cold environment, as discussed below.

In one embodiment, plugs 116 can attach to said power source 208 and provide electricity for running said surface sanitizing system 100. Said power lines 114 can attach plugs 116 to ion generation power module 112. Said ion generation power module 112 can generate sufficient voltage and electrical inputs, as discussed in the references incorporated by reference herein. Said two or more brush cables 110 can attach said ion generation power module 112 to said two brushes 108. Said female containment portions 104 can hold said two brushes 108 within a portion of brush container 102. Said two brushes 108 can attach to a portion of two or more brush cables 110, as discussed below. Said brush container 102 can selectively clip into mounting clip 106. Said mounting clip 106 can selectively attach to a portion of said ice maker 202.

In one embodiment, said surface sanitizing system 100 can be adapted to food grade environments such as freezers (walk in or reach in), raw food storage, and proofers.

In one embodiment, wires in said surface sanitizing system 100 can comprise NSF/FDA CFR 21 food grade wires. Nylon materials can be used for food grade injection molded parts. Further, all connectors and heat shrink can comprise food grade materials, as is known in the art.

Figure 2A:
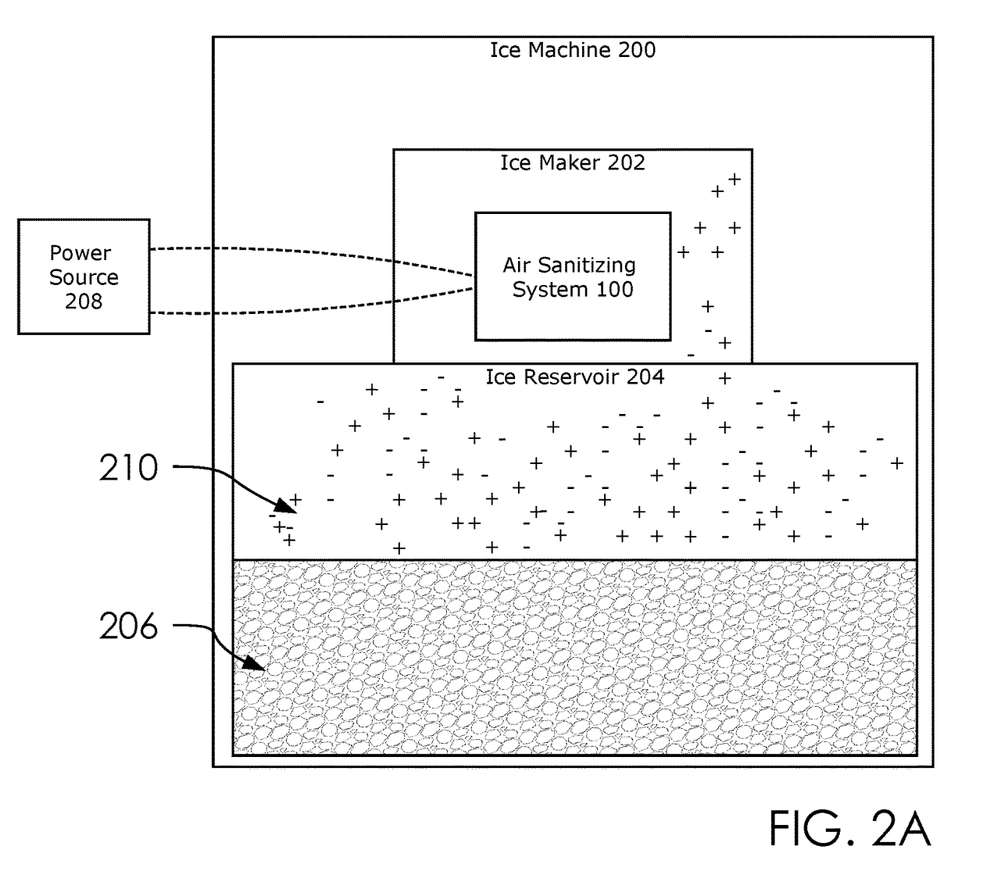
FIG. 2A illustrates a block diagram view of ice machine 200.

FIG. 2A illustrates a block diagram view of ice machine 200.

Figure 2B:
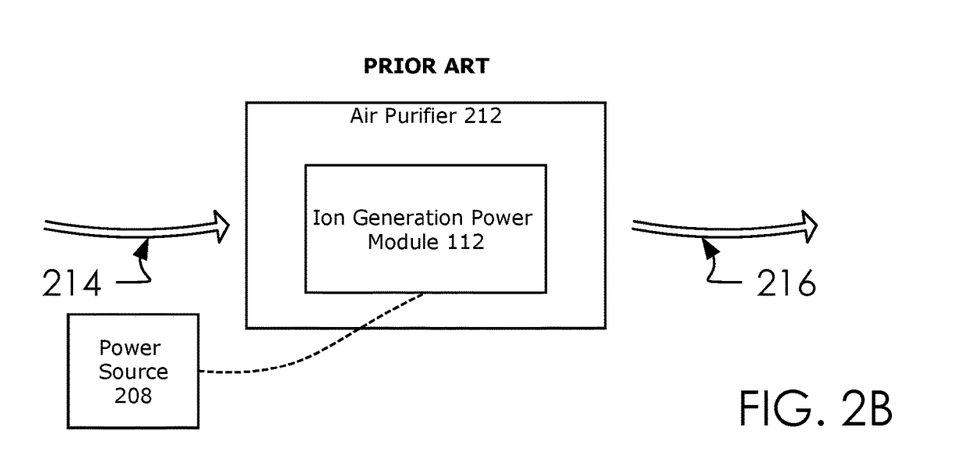
FIG. 2B illustrates a flow chart view of air purifier 212 as used in the prior art.

FIG. 2B illustrates a flow chart view of air purifier 212 as used in the prior art.

In one embodiment, said ice machine 200 can comprise said ice maker 202 and said ice reservoir 204.

In one embodiment, said air purifier 212 can comprise said air in 214 and said air out 216.

In one embodiment, said surface sanitizing system 100 can comprise said power source 208 and said bipolar ions 210.

In one embodiment, said brush container 102 can comprise said bipolar ions 210.

Bipolar Ionization is a process in which the decomposition of gas molecules into atoms is effected by the aid of high energy sources. The natural source for this high energy is UV solar radiation and soil radioactivity.

By including surface sanitizing system 100 within a portion of ice machine 200, such as ice maker 202, said bipolar ions 210 can be released into ice machine 200 and thereby ensure cleanliness of said ice 206.

Referring to FIG. 2B, we note that ion generation power module 112 has been used in air purifier 212 in the past. Note that in this case said air in 214 and air out 216 are the focus of those systems. Whereas, surface sanitizing system 100 is for use in a mostly closed system without large amounts of air in and out, relatively speaking.

In one embodiment, said surface sanitizing system 100 can generate 200 M positive and 200 M negative charged ions per cubic centimeter when 1 inch away from said two brushes 108; however, density can decrease further away from said two brushes 108.

As illustrated, two lines are shown between power source 208 and surface sanitizing system 100; in one embodiment, said power source 208 can send 6000 KV (positive and negative) into said surface sanitizing system 100.

Figure 3:
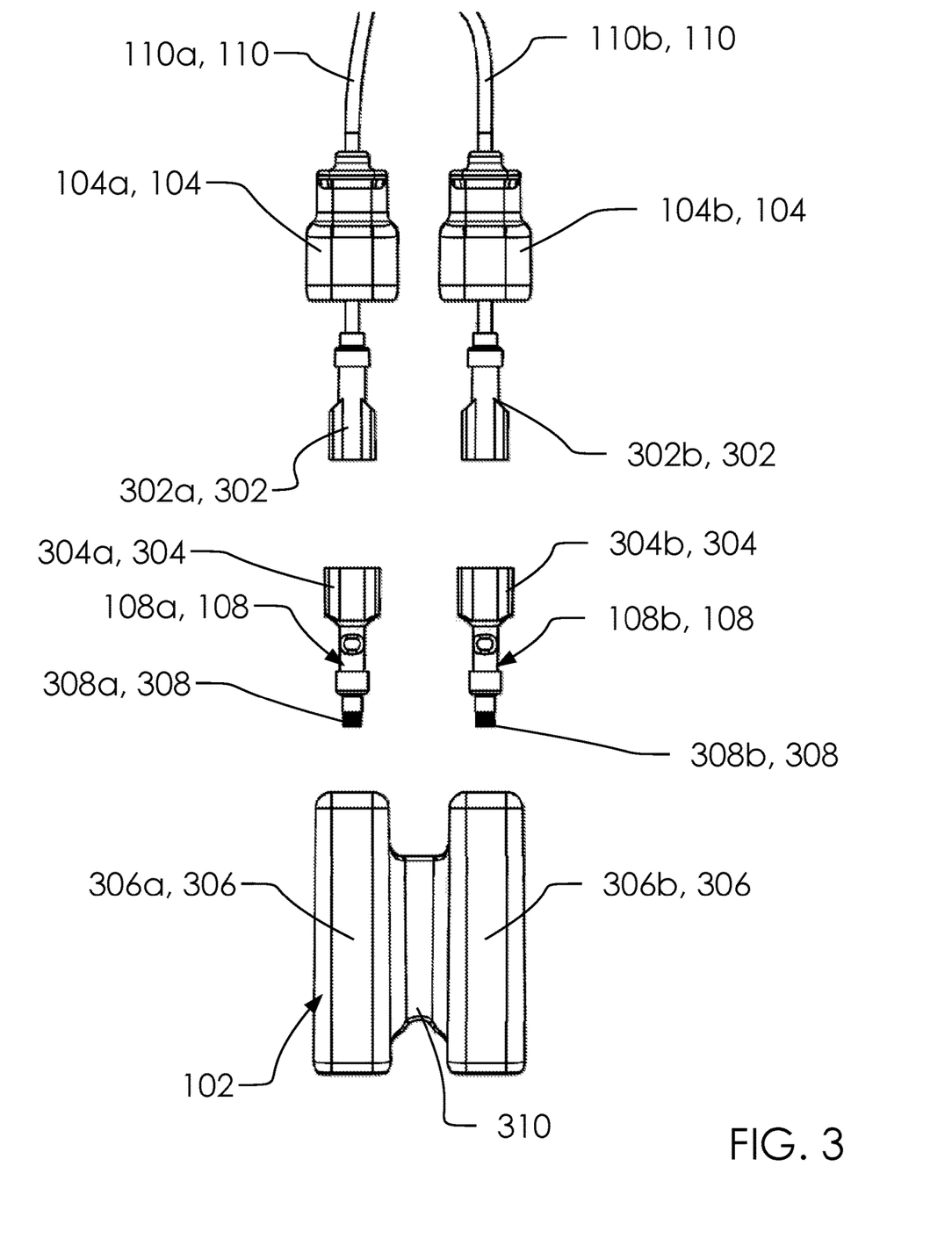
FIG. 3 illustrates an elevated top side view of said two or more brush cables 110, said female containment portions 104, said plugs 302, said sockets 304, and said brush container 102.

FIG. 3 illustrates an elevated top side view of said two or more brush cables 110, said female containment portions 104, said plugs 302, said sockets 304, and said brush container 102.

In one embodiment, said plugs 302 can comprise said first plug 302*a* and said second plug 302*b*.

In one embodiment, said sockets 304 can comprise said first socket 304*a* and said second socket 304*b*.

In one embodiment, said two sides 306 can comprise said first side 306*a* and said second side 306*b*.

In one embodiment, said brushes 308 can comprise said first brush 308*a* and said second brush 308*b*.

In one embodiment, said brush container 102 can comprise said second socket 304*b*, said two sides 306 and said bridge 310.

In one embodiment, said two brushes 108 can comprise said second plug 302*b*, said sockets 304, said second side 306*b* and said brushes 308.

In one embodiment, said two or more brush cables 110 can comprise said plugs 302.

Focusing now on the interaction of two or more brush cables 110, two brushes 108 and brush container 102. A portion of said two or more brush cables 110 can fit through a portion of female containment portions 104. In one embodiment, two or more brush cables 110 can comprise plugs 302 at one end for selectively mating with two brushes 108. In one embodiment, plugs 302 can selectively mate with sockets 304 of two brushes 108. Said two brushes 108 can comprise sockets 304 at one end and brushes 308 at another end. Accordingly, two or more brush cables 110 can be attached to two brushes 108 and the resulting assembly can end with said brushes 308 extending from the end thereof.

In one embodiment, brushes 308 may need protection within a setting such as said ice machine 200. In one embodiment, a portion of brushes 308 can be inserted into two sides 306. Accordingly, since brushes 308 are separated and shielded within two sides 306, said surface sanitizing system 100 can function more efficiently and safely.

brush container 102 can comprise two sides 306. Said two sides 306 can comprise first side 306*a* and second side 306*b*. Said two sides 306 can be separate chambers being attached to one another with bridge 310. Said two sides 306 can be substantially parallel.

In one embodiment, said brushes 308 can be replaced regularly for maintenance. If used in a dinning establishment, the brushes might get caked in grease, it might be a best practice to remove and replace them. One benefit of said surface sanitizing system 100, is easy access to said sockets 304 and said brushes 308 within said brush container 102 for replacement.

In one embodiment, said brushes 308 can comprise non-food grade materials, accordingly, said brush container 102 can provide certified clean use of said surface sanitizing system 100 despite using said brushes 308 in this condition.

In one embodiment, said brushes 308 can be carefully centered in said two sides 306 of said brush container 102. This feature can encourage high production.

Herein, said surface sanitizing system 100 can comprise nylon materials which is not only food grade, but suitable for electrically charged elements as nylon is anti-static.

Figure 4A:
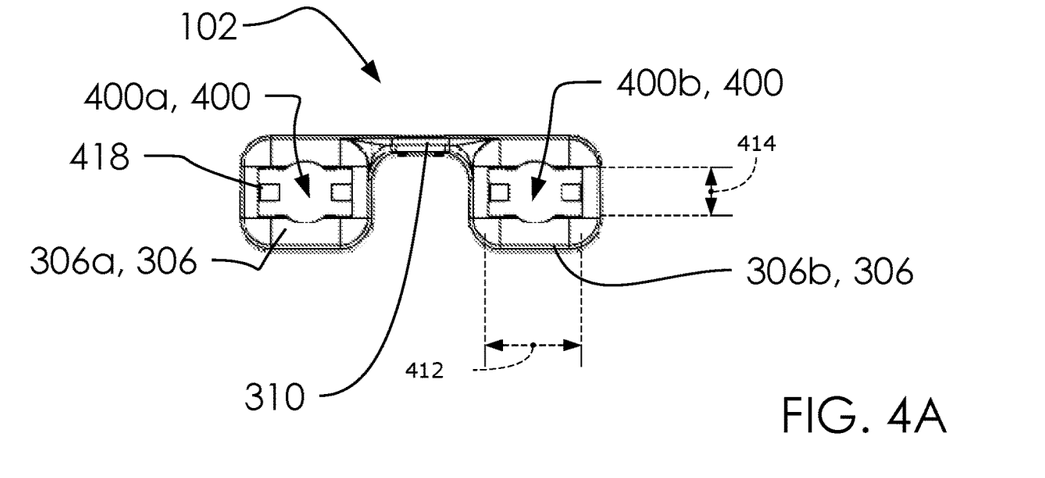
FIG. 4A illustrates an elevated front side view of brush container 102.

FIG. 4A illustrates an elevated front side view of brush container 102.

Figure 4B:
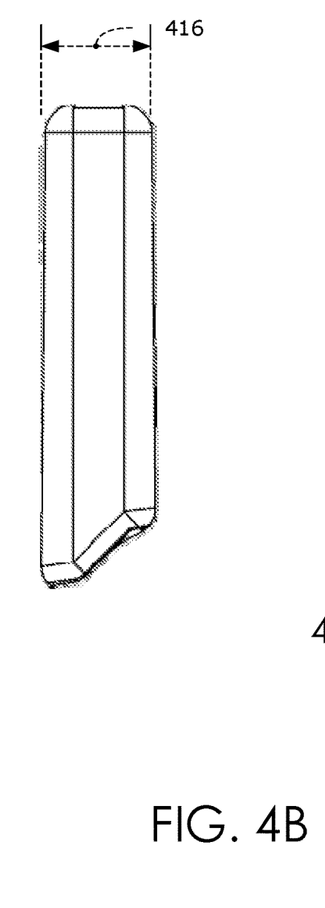
FIG. 4B illustrates an elevated first side view of brush container 102.

FIG. 4B illustrates an elevated first side view of brush container 102.

Figure 4C:
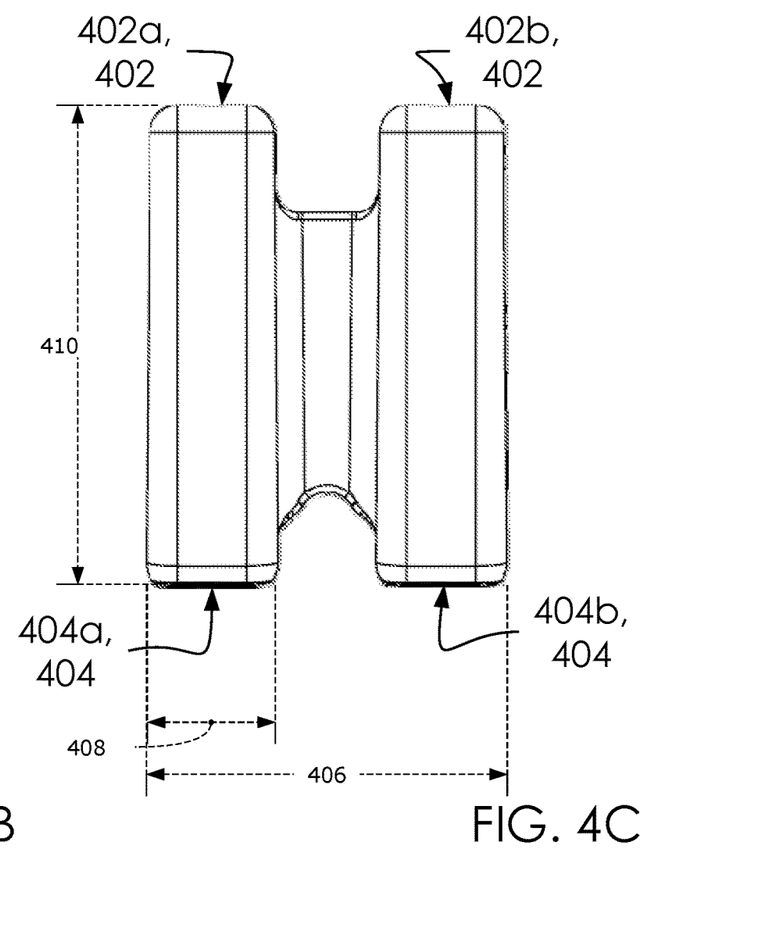
FIG. 4C illustrates an elevated top side view of brush container 102.

FIG. 4C illustrates an elevated top side view of brush container 102.

In one embodiment, said sockets 400 can comprise said first socket 400a, said second socket 400b, said socket width 412 and said socket height 414.

In one embodiment, said brush sockets 402 can comprise said first brush socket 402a and said second brush socket 402b.

In one embodiment, said emission sockets 404 can comprise said first emission socket 404a and said second emission socket 404b.

In one embodiment, said brush container 102 can comprise said sockets 400, said second socket 400b, said brush sockets 402, said second brush socket 402b, said emission sockets 404, said width 406, said length 410, said height 416 and said stops 418.

In one embodiment, said two sides 306 can comprise said width 408.

Said brush container 102 can comprise sockets 400 for holding a portion of two brushes 108. first socket 400a and second socket 400b can comprise substantially parallel tunnels for holding said two brushes 108. Said sockets 400 can comprise brush sockets 402 and emission sockets 404, as illustrated. In one embodiment, a portion of two brushes 108 can inserted into brush sockets 402 and remain inserted therein during operation of surface sanitizing system 100.

Said bridge 310 can be adapted for selectively attaching to mounting clip 106, as discussed below.

Concerning said brush container 102, the rake of the holster can keep said brushes 308 dry and allow said bipolar ions 210 to flow out of the containment.

In one embodiment, the radius of parts of said brush container 102 can comprise at least 0.125" to allow for easy cleaning.

In one embodiment, said stops 418 can be arranged on either side of said sockets 400, as illustrated. In one embodiment, said sockets 400 can prevent said brushes 308 from entering said brush container 102 too far and ensure centering and location.

Figure 5:
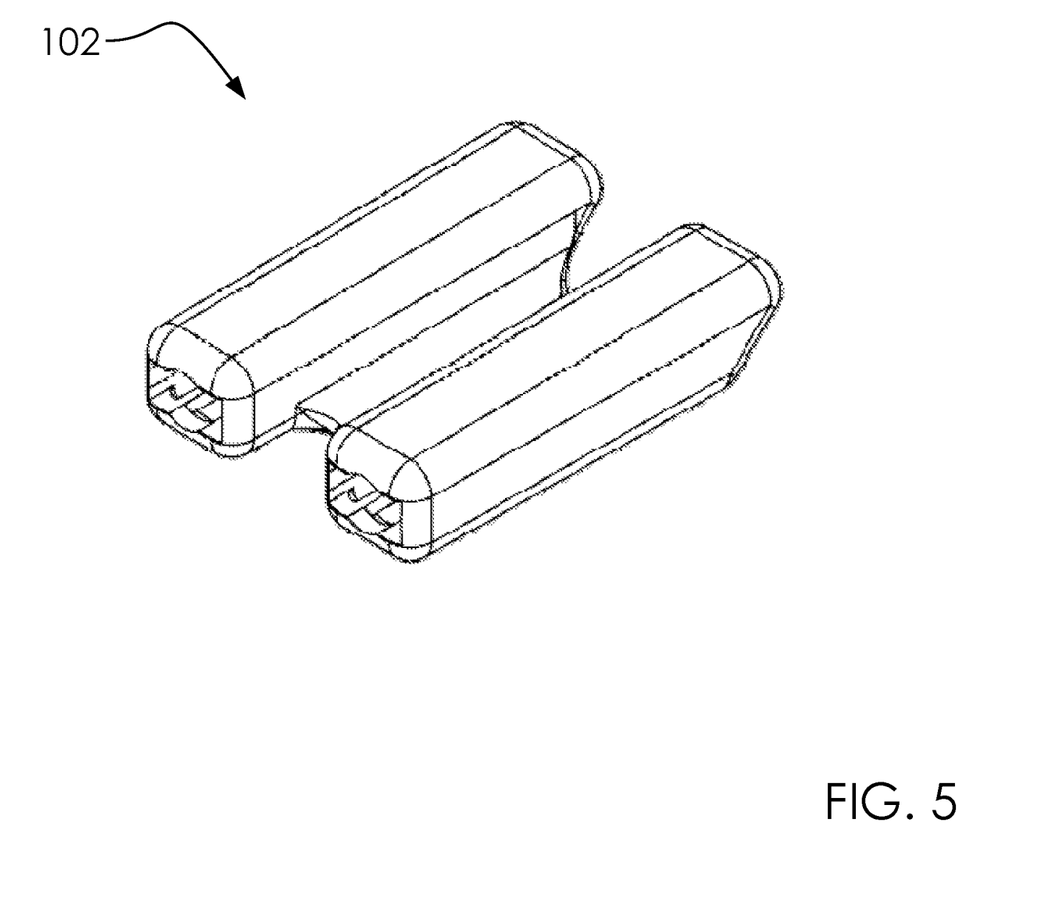
FIG. 5 illustrates a perspective overview view of brush container 102.

FIG. 5 illustrates a perspective overview view of brush container 102.

Figure 6A:
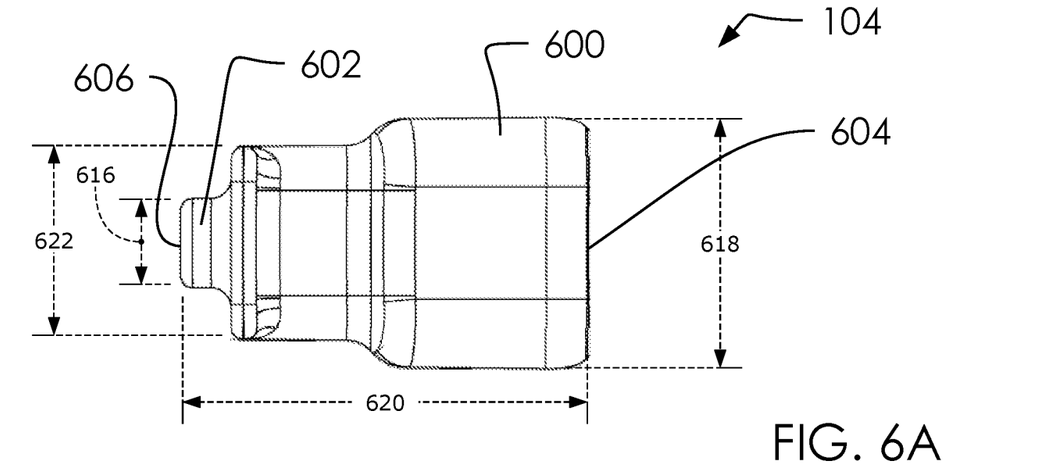
FIG. 6A illustrates an elevated front side view of female containment portions 104.

FIG. 6A illustrates an elevated front side view of female containment portions 104.

Figure 6B:
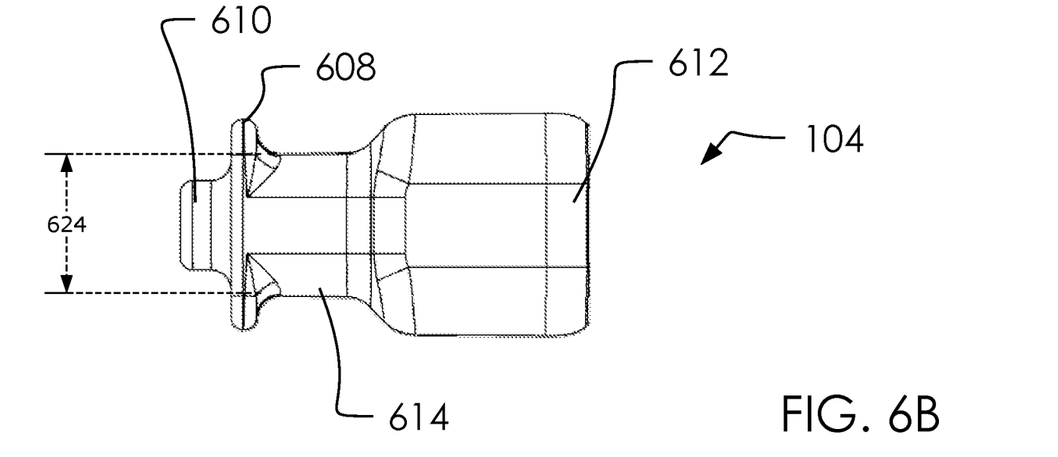
FIG. 6B illustrates an elevated top side view of female containment portions 104.

FIG. 6B illustrates an elevated top side view of female containment portions 104.

Figure 6C:
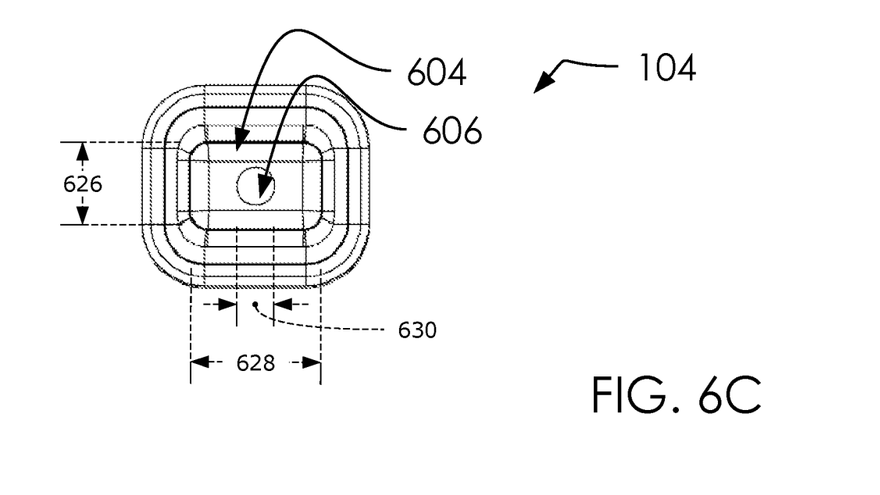
FIG. 6C illustrates an elevated first side view of female containment portions 104.

FIG. 6C illustrates an elevated first side view of female containment portions 104.

In one embodiment, said brush containment portion 600 can comprise said width 618.

In one embodiment, said line containment portion 602 can comprise said width 616.

In one embodiment, said brush aperture 604 can comprise said height 626 and said width 628.

In one embodiment, said line aperture 606 can comprise said diameter 630.

In one embodiment, said neck 614 can comprise said width 622 and said height 624.

In one embodiment, said female containment portions 104 can comprise said brush containment portion 600, said line containment portion 602, said brush aperture 604, said line aperture 606, said grip 608, said first end 610, said second end 612, said neck 614 and said length 620.

In one embodiment, brush aperture 604 can receive a portion of brush sockets 402 of brush container 102; wherein, said two brushes 108 can be encased in portions of brush container 102 and female containment portions 104. Said height 626 and width 628 of female containment portions 104 can be large enough to accommodate and selectively hold a portion of brush sockets 402 having width 408 and height 416; wherein, brush sockets 402 comprises an internal fitting piece and female containment portions 104 comprise and external fitting piece.

In one embodiment, line aperture 606 can comprise a diameter large enough to hold a portion of two or more brush cables 110 within line containment portion 602 of female containment portions 104.

In one embodiment, a portion of two or more brush cables 110 passes through line aperture 606, and extends toward brush aperture 604; two brushes 108 attach to two or more brush cables 110 within a portion of female containment portions 104; said brush containment portion 600 of female containment portions 104 attaches to a portion of brush container 102.

grip 608 can comprise a grip for pulling female containment portions 104 relative to two or more brush cables 110 and/or brush container 102.

In one embodiment, said female containment portions 104 can be configured to tight tolerances around said two or more brush cables 110. In one embodiment, said tight tolerances can allow for cleaning and access but minimal inputs.

Figure 7A:
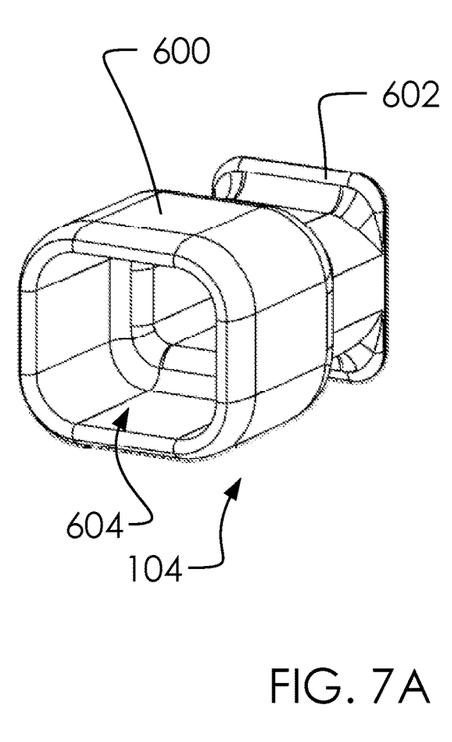
FIG. 7A illustrates a perspective front side view of female containment portions 104.

FIG. 7A illustrates a perspective front side view of female containment portions 104.

Figure 7B:
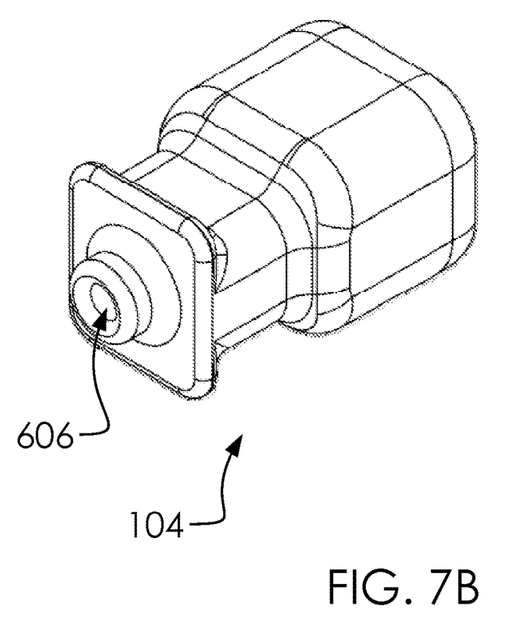
FIG. 7B illustrates a perspective back side view of female containment portions 104.

FIG. 7B illustrates a perspective back side view of female containment portions 104.

Figure 8:
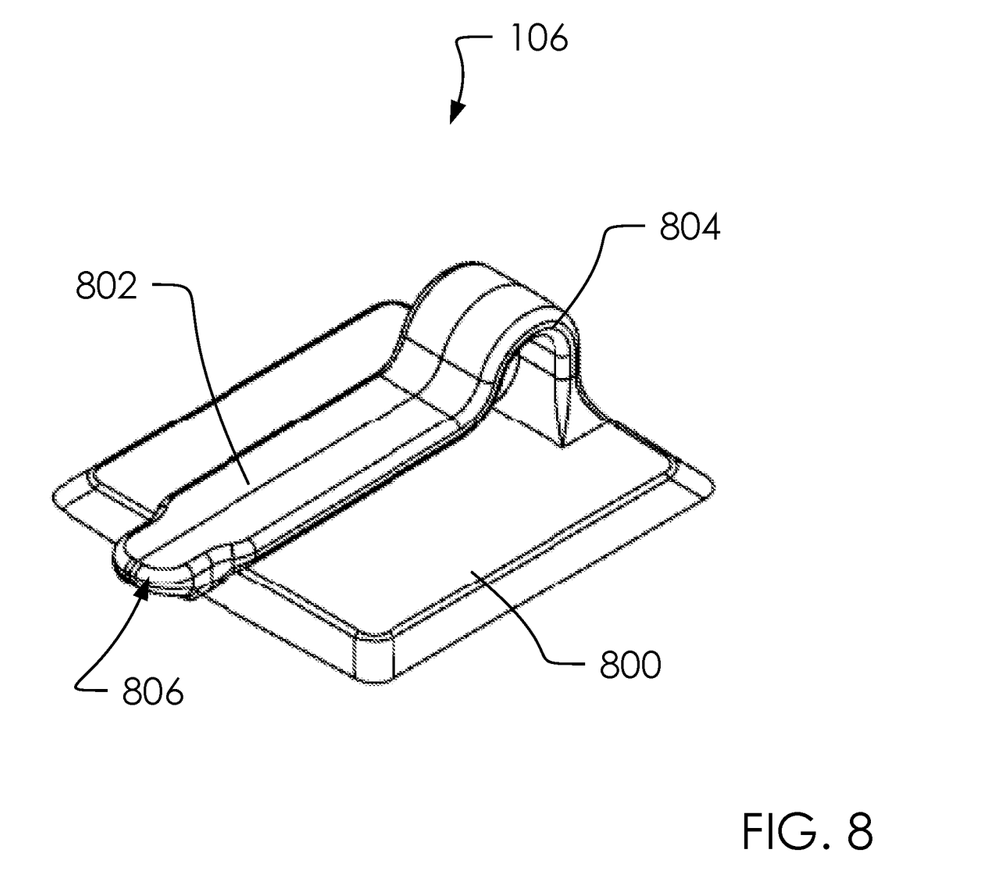
FIG. 8 illustrates a perspective overview view of mounting clip 106.

FIG. 8 illustrates a perspective overview view of mounting clip 106.

In one embodiment, said mounting clip 106 can comprise said base 800, said clip body 802, said bridge 804 and said clip head 806.

In one embodiment, mounting clip 106 can be adapted to attaching to a portion of ice machine 200, and selectively holding a portion of brush container 102 with said clip body 802.

In one embodiment, base 800 can comprise a substantially planar portion of mounting clip 106 for attaching to a portion of ice machine 200. Said bridge 804 can extend up and substantially perpendicular to the planar surface of 800, as illustrated. In one embodiment, said clip body 802 can extend across a portion of base 800; and clip head 806 can create a gripping head at a far end of clip body 802 from bridge 804, as illustrated.

In one embodiment, said surface sanitizing system 100 can be configured to keep said mounting clip 106 in said ice machine 200 but allowing said brush container 102 to be removed and run through a sanitization cycle in a cleaning machine such as a dish washer.

Figure 9A:
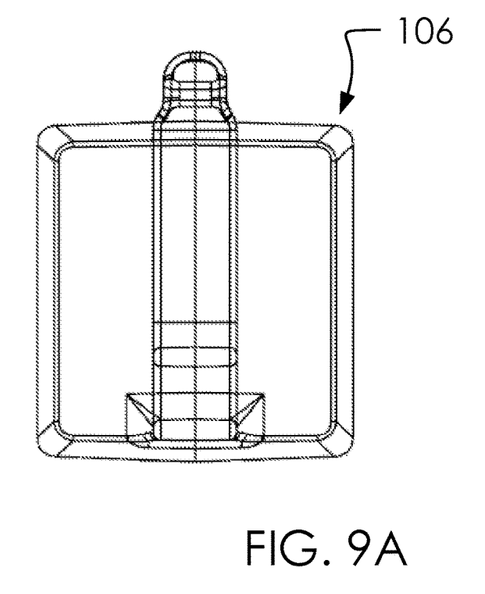
FIG. 9A illustrates an elevated top side view of mounting clip 106, rendered in transparent wire frame.

FIG. 9A illustrates an elevated top side view of mounting clip 106, rendered in transparent wire frame.

Figure 9B:
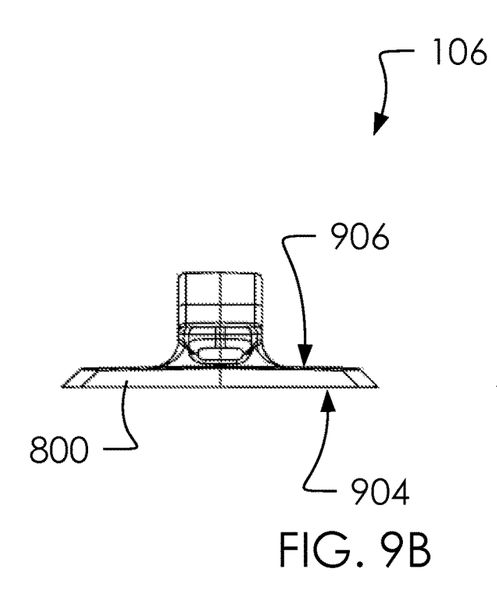
FIG. 9B illustrates an elevated front side view of mounting clip 106.

FIG. 9B illustrates an elevated front side view of mounting clip 106.

Figure 9C:
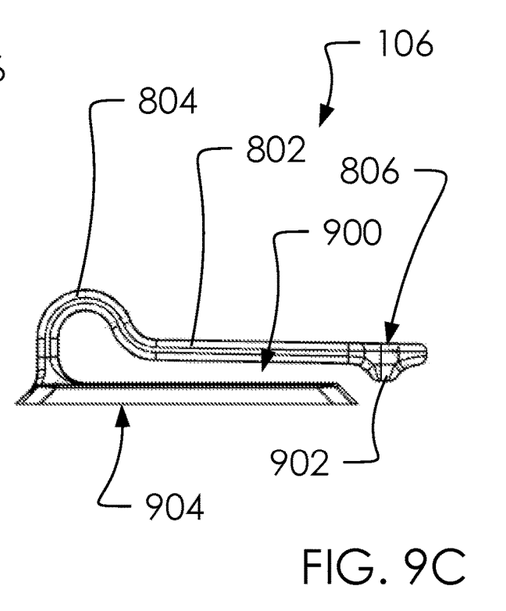
FIG. 9C illustrates an elevated first side view of mounting clip 106.

FIG. 9C illustrates an elevated first side view of mounting clip 106.

In one embodiment, said mounting clip 106 can comprise said clip enclosure 900.

In one embodiment, said plugs 116 can comprise said top surface 906.

In one embodiment, said base 800 can comprise said bottom surface 904 and said top surface 906.

In one embodiment, said clip body 802 can comprise said enclosure bump 902.

In one embodiment, base 800 can comprise top surface 906 and bottom surface 904. In one embodiment, bottom surface 904 can comprise adhesive for attaching mounting clip 106 to a portion of ice machine 200.

In one embodiment, clip head 806 can comprise enclosure bump 902; wherein, said clip enclosure 900 being between enclosure bump 902, clip body 802, bridge 804 and top surface 906 can be selectively accessed through enclosure bump 902, as is known in the art. In one embodiment, attaching a portion of brush container 102 to mounting clip 106 can comprise sliding a portion of bridge 310 under enclosure bump 902 and into clip enclosure 900, and pressing a portion of clip body 802 into bridge 310.

In one embodiment, said bottom surface 904 can comprise food grade adhesive. In one embodiment, said bottom surface 904 can not be use with mechanical fasteners to ensure cleanliness.

In one embodiment, said enclosure bump 902 be increased and decreased to ensure bonding between said mounting clip 106 and said ice machine 200.

Figure 10:
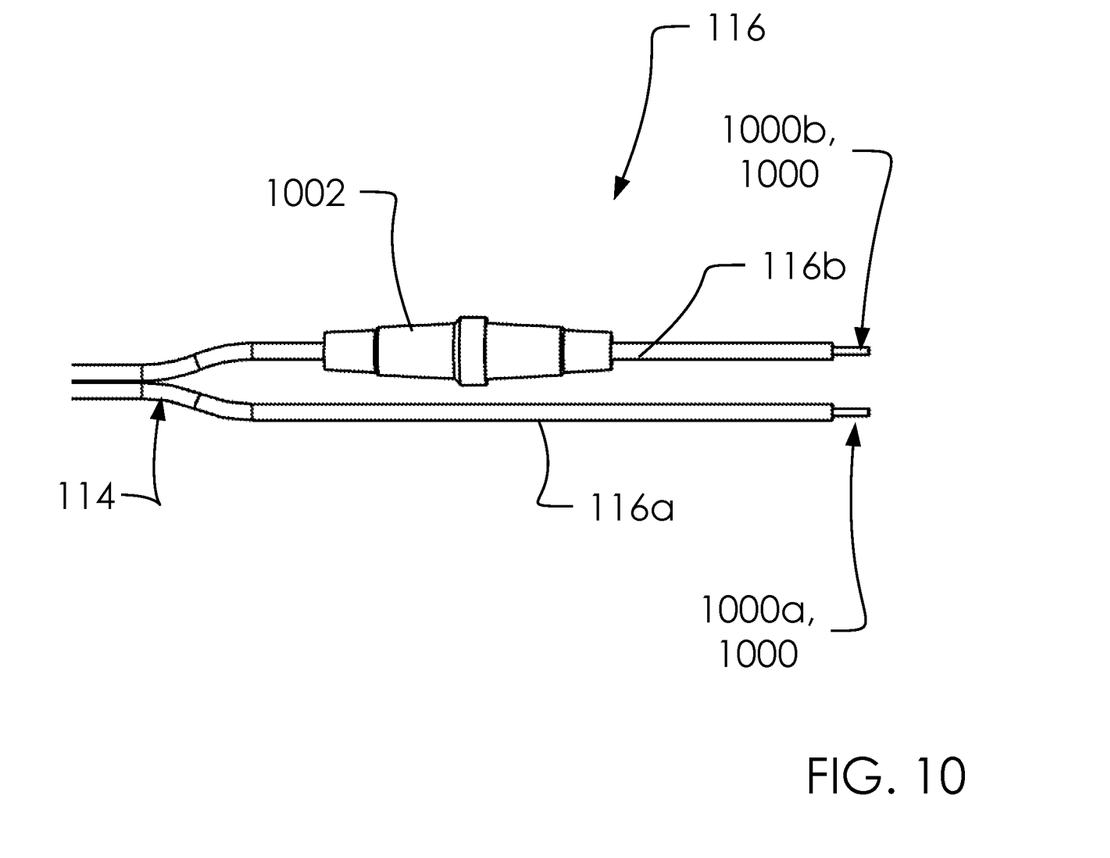
FIG. 10 illustrates an elevated overview view of plugs 116.

FIG. 10 illustrates an elevated overview view of plugs 116.

In one embodiment, said wires 1000 can comprise said first wire 1000a, said second wire 1000b and said inline fuse 1002.

In one embodiment, said plugs 116 can comprise said wires 1000.

Said plugs 116 can be used as is known in the art.

Figure 11:
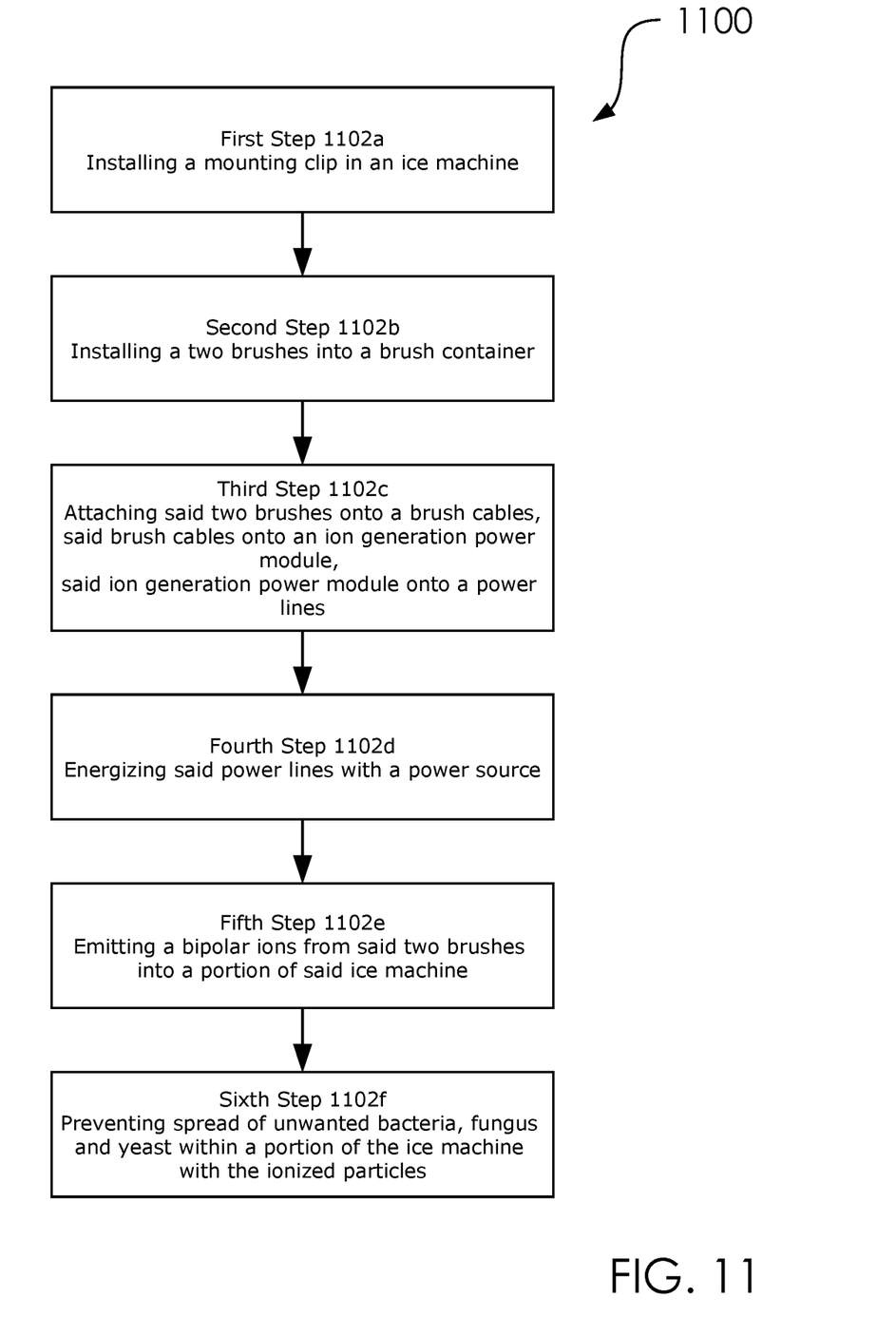
FIG. 11 illustrates a flow chart view of said ice machine cleaning method 1100.

FIG. 11 illustrates a flow chart view of said ice machine cleaning method 1100.

In one embodiment, said ice machine cleaning method 1100 can comprise said one or more steps 1102.

In one embodiment, said one or more steps 1102 can comprise said first step 1102a, said second step 1102b, said third step 1102c, said fourth step 1102d, said fifth step 1102e and said sixth step 1102f.

In one embodiment, said surface sanitizing system 100 can comprise said ice machine cleaning method 1100.

In one embodiment, said two or more brush cables 110 can comprise said ice machine cleaning method 1100.

With regard to one or more steps 1102: first step 1102a can comprise installing mounting clip 106 into a portion of ice machine 200; second step 1102b can comprise installing a portion of two brushes 108 into brush container 102; said third step 1102c can comprise attaching two brushes 108 to two or more brush cables 110, said two or more brush cables 110 to ion generation power module 112, said ion generation power module 112 to power lines 114, power lines 114 to plugs 116, and said plugs 116 to power source 208; said fourth step 1102d can comprise energizing plugs 116 with power source 208; said fifth step 1102e can comprise emitting said bipolar ions 210 with two brushes 108 into a portion of ice machine 200; and said sixth step 1102f can comprise preventing the spread of unwanted bacteria, fungus, and yeast within a portion of ice machine 200 with said bipolar ions 210.

Figure 12:
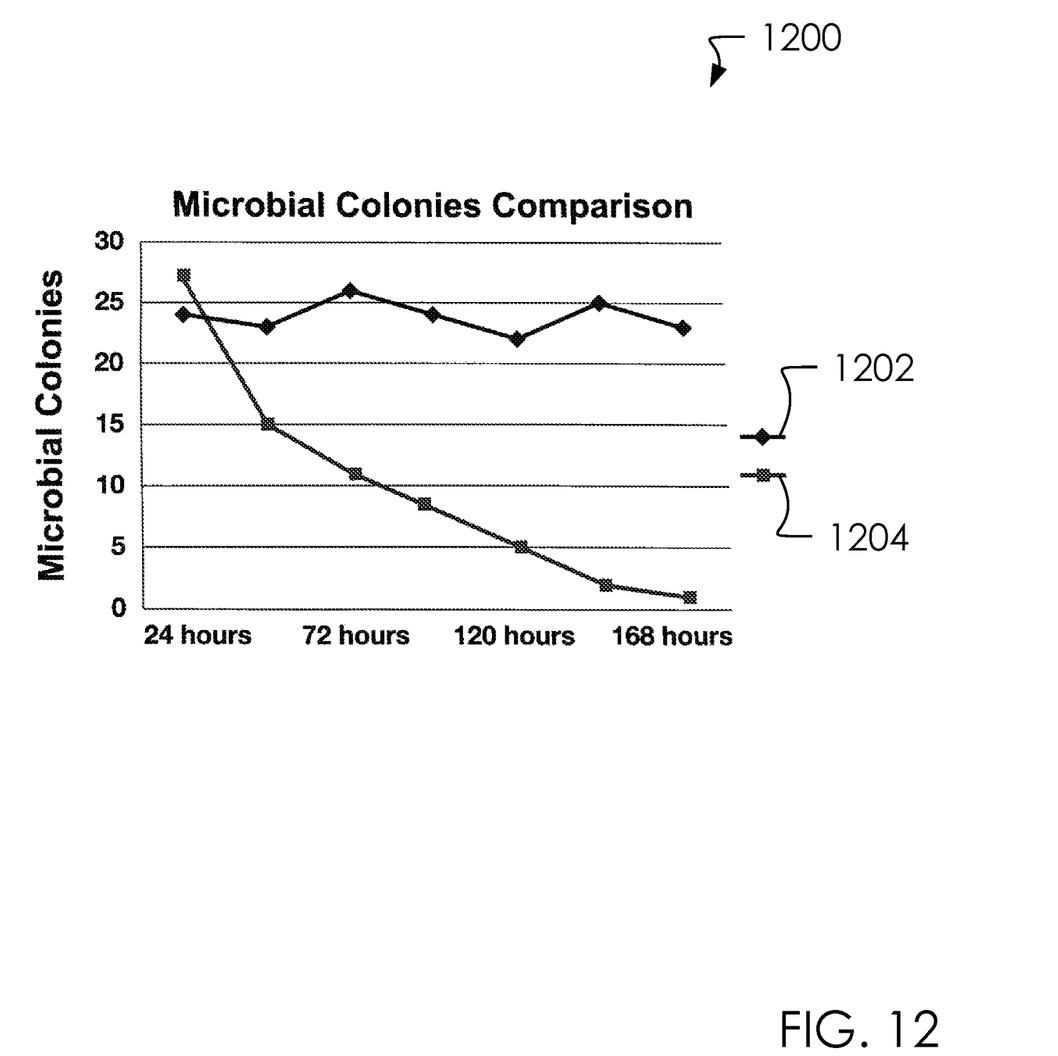
FIG. 12 illustrates a chart 1200 showing a first microbial colonies over time 1202 and a second microbial colonies over time 1204.

FIG. 12 illustrates a chart 1200 showing a first microbial colonies over time 1202 and a second microbial colonies over time 1204.

The following sentences are included for completeness of this disclosure with reference to the claims.

An surface sanitizing system 100 for cleaning a portion of an ice machine 200 with a bipolar ions 210, wherein, said surface sanitizing system 100 comprises a plugs 116, a power lines 114, an ion generation power module 112, a two or more brush cables 110, a two brushes 108 a brush container 102 and a mounting clip 106. Said plugs 116 selectively attaches to a power source 208 and provides electricity for running said surface sanitizing system 100. Said power lines 114 selectively attach said plugs 116 to said ion generation power module 112. Said two or more brush cables 110 selectively attach said ion generation power module 112 to said two brushes 108. A female containment portions 104 selectively holds said two brushes 108 within a portion of said brush container 102. Said two brushes 108 selectively attach to a portion of said two or more brush cables 110. Said brush container 102 selectively clips into said mounting clip 106. Said mounting clip 106 selectively attaches to a portion of an ice maker 202. Said surface sanitizing system 100 comprising a one or more steps 1102 comprising installing said mounting clip 106 into a portion of said ice machine 200, installing a portion of said two brushes 108 into said brush container 102, attaching said two brushes 108 to said two or more brush cables 110, said two or more brush cables 110 to said ion generation power module 112, said ion generation power module 112 to said power lines 114, said power lines 114 to said plugs 116, and said plugs 116 to said power source 208, energizing said plugs 116 with said power source 208, emitting said bipolar ions 210 with said two brushes 108 into a portion of said ice machine 200, and preventing the spread of unwanted bacteria, fungus, and yeast within a portion of said ice machine 200 with said bipolar ions 210. An surface sanitizing system 100 for cleaning a portion of an ice machine 200 with a bipolar ions 210, wherein, Said surface sanitizing system 100 comprises a plugs 116, a power lines 114, an ion generation power module 112, a two or more brush cables 110, a two brushes 108 and a mounting clip 106. Said plugs 116 selectively attaches to a power source 208 and provides electricity for running said surface sanitizing system 100. Said power lines 114 selectively attach said plugs 116 to said ion generation power module 112. Said two or more brush cables 110 selectively attach said ion generation power module 112 to said two brushes 108. Said two brushes 108 selectively attach to a portion of said two or more brush cables 110.

Said surface sanitizing system 100 further comprises a brush container 102. A female containment portions 104 selectively holds said two brushes 108 within a portion of said brush container 102. Said mounting clip 106 selectively attaches to a portion of an ice maker 202. Said surface sanitizing system 100 comprising a one or more steps 1102 comprising installing said mounting clip 106 into a portion of said ice machine 200, installing a portion of said two brushes 108 into said brush container 102, attaching said two brushes 108 to said two or more brush cables 110, said two or more brush cables 110 to said ion generation power module 112, said ion generation power module 112 to said power lines 114, said power lines 114 to said plugs 116, and said plugs 116 to said power source 208, energizing said plugs 116 with said power source 208, emitting said bipolar ions 210 with said two brushes 108 into a portion of said ice machine 200, and preventing the spread of unwanted bacteria, fungus, and yeast within a portion of said ice machine 200 with said bipolar ions 210.

Said surface sanitizing system 100 further comprises a brush container 102. A female containment portions 104 selectively holds said two brushes 108 within a portion of said brush container 102. Said mounting clip 106 selectively attaches to a portion of an ice maker 202.

Said brush container 102 selectively clips into said mounting clip 106.

Said mounting clip 106 selectively attaches to a portion of said ice maker 202. Said surface sanitizing system 100 is configured to protect a portion of said ice machine 200 by: installing said mounting clip 106 into a portion of said ice machine 200, installing a portion of said two brushes 108 into said brush container 102, attaching said two brushes 108 to said two or more brush cables 110, said two or more brush cables 110 to said ion generation power module 112, said ion generation power module 112 to said power lines 114, said power lines 114 to said plugs 116, and said plugs 116 to said power source 208, energizing said plugs 116 with said power source 208, emitting said bipolar ions 210 with said two brushes 108 into a portion of said ice machine 200, and preventing the spread of unwanted bacteria, fungus, and yeast within a portion of said ice machine 200 with said bipolar ions 210. An ice machine cleaning method 1100 for cleaning a portion of an ice machine 200 with a bipolar ions 210 generated by an surface sanitizing system 100. Comprising Installing a mounting clip 106 of said surface sanitizing system 100 into a portion of said ice machine 200. Installing a portion of a two brushes 108 into a brush container 102. Attaching said two brushes 108 to a two or more brush cables 110, said two or more brush cables 110 to an ion generation power module 112, said ion generation power module 112 to a power lines 114, said power lines 114 to a plugs 116, and said plugs 116 to a power source 208. Energizing said plugs 116 with said power source 208. Emitting said bipolar ions 210 with said two brushes 108 into a portion of said ice machine 200. Preventing the spread of unwanted bacteria, fungus, and yeast within a portion of said ice machine 200 with said bipolar ions 210. Wherein said surface sanitizing system 100 comprises said plugs 116, said power lines 114, said ion generation power module 112, said two or more brush cables 110, said two brushes 108 said brush container 102 and said mounting clip 106. Wherein said plugs 116 selectively attaches to said power source 208 and provides electricity for running said surface sanitizing system 100. Wherein said power lines 114 selectively attach said plugs 116 to said ion generation power module 112. Wherein said two or more brush cables 110 selectively attach said ion generation power module 112 to said two brushes 108. Wherein a female containment portions 104 selectively holds said two brushes 108 within a portion of said brush container 102. Wherein said mounting clip 106 selectively attaches to a portion of an ice maker 202.

Selectively clipping said brush container 102 into said mounting clip 106.

Selectively attaching said two brushes 108 to a portion of said two or more brush cables 110.

Various changes in the details of the illustrated operational methods are possible without departing from the scope of the following claims. Some embodiments may combine the activities described herein as being separate steps. Similarly, one or more of the described steps may be omitted, depending upon the specific operational environment the method is being implemented in. It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

The invention claimed is:

1. A surface sanitizing system for cleaning a portion of an ice machine with a bipolar ions, wherein, said surface sanitizing system comprises a plugs, a power lines, an ion generation power module, a two or more brush cables, a two brushes, a brush container and a mounting clip; said plugs selectively attaches to a power source and provides electricity for running said surface sanitizing system; said power lines selectively attach said plugs to said ion generation power module; said two or more brush cables selectively attach said ion generation power module to said two brushes; a female containment portions selectively holds said two brushes within a portion of said brush container; said two brushes selectively attach to a portion of said two or more brush cables; said brush container selectively clips into said mounting clip; said mounting clip selectively attaches to a portion of an ice maker; and said surface sanitizing system comprising a one or more steps comprising installing said mounting clip into a portion of said ice machine, installing a portion of said two brushes into said brush container, attaching said two brushes to said two or more brush cables, said two or more brush cables to said ion generation power module, said ion generation power module to said power lines, said power lines to said plugs, and said plugs to said power source, energizing said plugs with said power source, emitting said bipolar ions with said two brushes into a portion of said ice machine, and preventing the spread of unwanted bacteria, fungus, and yeast within a portion of said ice machine with said bipolar ions.

2. A surface sanitizing system for cleaning a portion of an ice machine with a bipolar ions, wherein,
said surface sanitizing system comprises a plugs, a power lines, an ion generation power module, a two or more brush cables, a two brushes and a mounting clip;
said plugs selectively attaches to a power source and provides electricity for running said surface sanitizing system;
said power lines selectively attach said plugs to said ion generation power module;
said two or more brush cables selectively attach said ion generation power module to said two brushes; and
said two brushes selectively attach to a portion of said two or more brush cables.

3. The surface sanitizing system from claim 2, wherein:
said surface sanitizing system further comprises a brush container;
a female containment portions selectively holds said two brushes within a portion of said brush container;

said mounting clip selectively attaches to a portion of an ice maker; and said surface sanitizing system comprising a one or more steps comprising     installing said mounting clip into a portion of said ice machine,     installing a portion of said two brushes into said brush container,     attaching said two brushes to said two or more brush cables, said two or more brush cables to said ion generation power module, said ion generation power module to said power lines, said power lines to said plugs, and said plugs to said power source,     energizing said plugs with said power source,     emitting said bipolar ions with said two brushes into a portion of said ice machine, and     preventing the spread of unwanted bacteria, fungus, and yeast within a portion of said ice machine with said bipolar ions.

4. The surface sanitizing system from claim 2, wherein:

said surface sanitizing system further comprises a brush container;

a female containment portions selectively holds said two brushes within a portion of said brush container; and said mounting clip selectively attaches to a portion of an ice maker.

5. The surface sanitizing system from claim 4, wherein:

said brush container selectively clips into said mounting clip.

6. The surface sanitizing system from claim 4, wherein:

said mounting clip selectively attaches to a portion of said ice maker; and said surface sanitizing system is configured to protect a portion of said ice machine by:

installing said mounting clip into a portion of said ice machine,     installing a portion of said two brushes into said brush container,     attaching said two brushes to said two or more brush cables, said two or more brush cables to said ion generation power module, said ion generation power module to said power lines, said power lines to said plugs, and said plugs to said power source,     energizing said plugs with said power source,     emitting said bipolar ions with said two brushes into a portion of said ice machine, and     preventing the spread of unwanted bacteria, fungus, and yeast within a portion of said ice machine with said bipolar ions.

7. An ice machine cleaning method for cleaning a portion of an ice machine with a bipolar ions generated by an surface sanitizing system, comprising:

installing a mounting clip of said surface sanitizing system into a portion of said ice machine;

installing a portion of a two brushes into a brush container;

attaching said two brushes to a two or more brush cables, said two or more brush cables to an ion generation power module, said ion generation power module to a power lines, said power lines to a plugs, and said plugs to a power source;

energizing said plugs with said power source;

emitting said bipolar ions with said two brushes into a portion of said ice machine;

preventing the spread of unwanted bacteria, fungus, and yeast within a portion of said ice machine with said bipolar ions;

wherein said surface sanitizing system comprises said plugs, said power lines, said ion generation power module, said two or more brush cables, said two brushes said brush container and said mounting clip;

wherein said plugs selectively attaches to said power source and provides electricity for running said surface sanitizing system;

wherein said power lines selectively attach said plugs to said ion generation power module;

wherein said two or more brush cables selectively attach said ion generation power module to said two brushes;

wherein a female containment portions selectively holds said two brushes within a portion of said brush container; and     wherein said mounting clip selectively attaches to a portion of an ice maker.

8. The ice machine cleaning method from claim 7, wherein:

selectively clipping said brush container into said mounting clip.

9. The ice machine cleaning method from claim 7, wherein:

selectively attaching said two brushes to a portion of said two or more brush cables.

\* \* \* \* \*